(12) United States Patent  
Auboiroux et al.

(10) Patent No.: US 9,199,100 B2  
(45) Date of Patent: Dec. 1, 2015

(54) ULTRASOUND TRANSDUCER FOR MEDICAL USE

(75) Inventors: Vincent Auboiroux, Annemasse (FR); Erik Dumont, Bordeaux (FR); Rares Vincent Salomir, Ambilly (FR)

(73) Assignee: IMAGE GUIDED THERAPY, Pessac (FR)

( * ) Notice: Subject to any disclaimer, the term of this patent is extended or adjusted under 35 U.S.C. 154(b) by 114 days.

(21) Appl. No.: 13/702,645

(22) PCT Filed: Jun. 7, 2011

(86) PCT No.: PCT/FR2011/051288  
§ 371 (c)(1),  
(2), (4) Date: May 2, 2013

(87) PCT Pub. No.: WO2011/154654  
PCT Pub. Date: Dec. 15, 2011

(65) Prior Publication Data  
US 2013/0211293 A1    Aug. 15, 2013

(30) Foreign Application Priority Data

Jun. 7, 2010   (FR) .................................. 10 54454

(51) Int. Cl.  
| A61H 1/00 | (2006.01) |
| A61H 1/02 | (2006.01) |
| A61H 5/00 | (2006.01) |
| A61N 7/02 | (2006.01) |
| G10K 11/32 | (2006.01) |
| H04R 31/00 | (2006.01) |
| A61B 8/00 | (2006.01) |
| A61N 7/00 | (2006.01) |

(52) U.S. Cl.  
CPC ................ *A61N 7/02* (2013.01); *A61B 8/4483* (2013.01); *G10K 11/32* (2013.01); *H04R 31/00* (2013.01); *A61N 2007/0078* (2013.01); *A61N 2007/0095* (2013.01); *A61N 2007/027* (2013.01); *Y10T 29/49005* (2015.01)

(58) Field of Classification Search  
USPC ........................... 600/407, 437–472; 601/2–3  
See application file for complete search history.

(56) References Cited

U.S. PATENT DOCUMENTS 5,922,962 A * 7/1999 Ishrak et al. .................... 73/632  
6,135,971 A * 10/2000 Hutchinson et al. .............. 601/3

(Continued)

FOREIGN PATENT DOCUMENTS

WO    2008/015521    2/2008

OTHER PUBLICATIONS

International Search Report dated Mar. 7, 2012, corresponding to PCT/FR2011/051288.

*Primary Examiner* — James Kish  
(74) *Attorney, Agent, or Firm* — Young & Thompson

(57) ABSTRACT

A phased-network ultrasound transducer for medical use, includes a single support (2) and a group of transducer elements (3) distributed randomly on the surface of the support (2), the transducer elements (3) being fixed. The group includes at least two sub-groups of transducer elements (3), each of the sub-groups having a different geometric point of convergence such as to focus an ultrasound energy in a different coverage volume (4, 5) such that the arrangement of the coverage volumes covers a target volume to be treated. In addition, the transducer includes control elements for controlling the transducer elements (3) independently of one another.

14 Claims, 2 Drawing Sheets

(56) References Cited

U.S. PATENT DOCUMENTS

| | | | |
|---|---|---|---|
| 6,488,630 B1* | 12/2002 | Hand et al. | 600/459 |
| 2011/0066032 A1* | 3/2011 | Vitek et al. | 600/459 |
| 2011/0251527 A1* | 10/2011 | Kushculey et al. | 601/2 |
| 2014/0180103 A1* | 6/2014 | Sinelnikov | 600/439 |

* cited by examiner

A-A

ULTRASOUND TRANSDUCER FOR MEDICAL USE

The present invention relates to a phased-array ultrasound transducer for medical use, notably for therapeutic applications. It also relates to a therapeutic treatment machine equipped with at least one such ultrasound transducer.

Methods for the non-invasive ablation of cancerous tissues through the use of focused high-intensity ultrasounds are known. These methods are based on the localized and remote raising of the temperature of the biological tissues in order to necrose the cancerous tissues without touching the surrounding tissues.

This local temperature rise is obtained by focusing ultrasounds in the biological tissues, the apparatus generating the ultrasound waves being positioned outside the human body.

It is known that the therapeutic effectiveness of the treatment is enhanced when the focused ultrasounds are concentrated at a focal point of small volume compared to a diffuse focal point, provided that all of the tumoral volume is covered by the displacement of this focal point.

An effective treatment device must therefore combine a focal point of small dimension and the means to displace this focal point in order to cover all of the target volume to be treated.

The focusing of ultrasounds can be obtained using a wide variety of transducers, notably in terms of form and of constituent materials.

A transducer that is very widely used thus has the form of a spherical skull cap and is produced from a piece of piezoelectric ceramic or a shaped piezocomposite structure. The benefit of such a transducer then lies in its capacity to naturally focus an ultrasound beam at the geometrical center of the spherical skull cap.

This type of transducer thus makes it possible to obtain a strong concentration of the ultrasounds at the focal point so as to induce a local temperature rise compatible with a heat treatment of the tissues.

However, when the therapeutic target is placed in a mobile organ such as the liver or kidney, which is displaced by a few centimeters during the respiratory cycle, the focal point has to not only be able to cover all of the target volume but also be able to accompany, at least partially, the movement of the target.

This partial tracking of the target to be treated imposes a strong limitation on the amplitude of displacement necessary to the focal point to treat all of the target volume.

A number of solutions have been proposed for increasing the volume covered by the focused ultrasounds.

The simplest technical solution consists in fixing the ultrasound transducer on a motorized positioning system in such a way that the position and/or the orientation of the transducer can be modified remotely.

This technique offers very great flexibility in the displacement of the focal point. It potentially allows for control of the displacement of the focal point so as to follow a target in a mobile organ throughout the respiratory cycle.

However, this solution presents major drawbacks when it is installed in a magnetic resonance imaging (MRI) device.

First of all, the mechanical bulk is significant in the restricted space of the magnet of the MRI device.

Perturbations of the MRI imaging are also observed which are linked to radiofrequency interferences due to the motor-drive system and perturbations of the temperature maps obtained by MRI phase imaging. The latter result from magnetic susceptibility variations linked to the displacements of the transducer within the magnetic field of the magnet.

Now, monitoring by imaging the patient during the therapeutic treatment is essential to guarantee the safety of the patient and ensure the reliability of the procedure. MRI imaging presents two major advantages in terms of monitoring heat ablation compared to the other imaging techniques that are available such as echography.

First of all, MRI imaging makes it possible to clearly visualize the tumor and the surrounding sensitive tissues, which is essential for optimum planning of the therapeutic treatment. Then, MRI provides a reliable temperature map throughout the target volume during the treatment, which makes it possible not only to visualize the heat ablation in real time but above all to adapt the treatment according to the response of the tissues.

In the document "IEEE Transactions on ultrasonics, ferroelectrics and frequency control", Vol. 36, No. 5, September 1989, EBBINI et al. introduced the concept of a phased array in which the ultrasound transducer is divided into a number of active elements, each of these active elements being excited by an excitation signal whose phase is individually controlled.

The position of the focal point can then be modified by applying an appropriate phase law to the elements that make up the transducer. This method is commonly called "beamforming", or even electronic deflection of the focal point, and is applied to the so-called phased arrays.

The formation of a coverage volume, also called accessible focusing area, by electronic deflection of the focal point of a matrix of transducer elements is thus disclosed. This coverage volume is characterized by an acoustic energy of the deflected focal point of at least 50% of the energy of the focal point at the point of geometrical convergence, which is the center of the spherical scull cap.

This document also teaches how to generate focusing "patterns" in the coverage volume. These "patterns" can, for example, be multiple focal points. To sum up, all the uses of a phased-array transducer (deflection and multi-focus) are described in this prior art document.

As an illustration, such ultrasound beamforming makes it possible to obtain a focusing from a planar support surface and allows the displacement of the focal point within a small area without mechanical displacement of the transducer, and with a much shorter response time than with a conventional motorized displacement system.

However, problems appear when the dividing up of the transducer into different active elements is too regular. Secondary focal points appear according to the position of the primary focal point. These secondary focal points, also called "grating lobes" (secondary lobes), can provoke temperature rises at undesirable points and thus detract from the use of phased-array transducers for heat ablation.

Progress has been made with the emergence of transducers whose elements are distributed pseudo-randomly on the support surface. This pseudo-random distribution limits the appearance of any undesirable hot spots during the electronic deflection of the beam, which explains why it is the type of transducer most commonly used today.

The main limitation of this type of ultrasound transducer remains the relatively small size of the coverage area of the focal point.

The electronic deflection is primarily limited by the radiation pattern of the individual emitters (inversely proportional to the diameter×frequency product) and depends on the geometry of the transducer, in particular the radius of curvature of the spherical skull cap. Bearing in mind that, at the working frequency, the emitted beam is directional, an attempt to focus far from the natural focal point will be reflected in a strong drop in effectiveness.

Typically, for a transducer of 13 cm radius of curvature, operating at a frequency of 1 MHz, with 256 circular elements of 6 mm diameter, the maximum deflection of the focal point is approximately 15 mm relative to the natural focal point (center of the spherical skull cap).

This coverage is compatible with the methods for compensating for small displacements of the organs in order to create a precise lesion, with no blurring effect induced by the movement, or to create a wider lesion in the case of immobile organs.

However, this method does not make it possible to treat a large volume in the presence of respiratory movement without having recourse to a mechanical displacement system.

The phased-array transducers, with elements scattered randomly on a concave surface, are generally not very dense. In practice, if the surface of the elements is too great relative to the surface of the transducer (>50%), the position of the elements becomes less random and, at the limit of a compact transducer or the surface of the elements approaches 70% of the surface of the transducer, the distribution of the elements becomes totally ordered with, consequently, the appearance of secondary focal points or lobes.

The present invention aims to overcome these various drawbacks by proposing an ultrasound transducer that is particularly simple in its design and in its operating mode, economical and that makes it possible to obtain a wider coverage area than with the techniques known from the prior art.

To this end, the invention relates to a phased-array ultrasound transducer for medical use, this transducer comprising a single support and a set of transducer elements distributed randomly on the surface of said support, said transducer elements being fixed.

According to the invention,
this set comprises at least two subsets of transducer elements, each of said subsets of transducer elements having a distinct point of geometrical convergence so as to focus an ultrasound energy in a distinct coverage volume such that the arrangement of said coverage volumes covers a target volume to be treated, and
control means for controlling said transducer elements independently of one another.

This ultrasound transducer advantageously makes it possible to define at least two distinct coverage volumes, which can be contiguous, or even present a cross check volume. It is thus possible to check the treatment of a target volume that is mobile between two extreme points, the range of displacement of this target volume being covered by distinct coverage volumes.

One of the benefits of this ultrasound transducer is consequently to increase the accuracy of the therapeutic treatment, by delivering the therapeutic dose within a treatment area covering the movement of a target volume without mechanical displacement of the transducer. The dynamic susceptibility artifacts in MRI imaging are thus avoided.

This ultrasound transducer also makes it possible to treat at one and the same time larger volumes of cancerous tissues for a fixed target.

This transducer also makes it possible to enhance the prediction of the dose actually deposited on the biological tissues since it is possible to be assured of a continuous effective treatment within the target volume to be treated.

The control means emit excitation signals that have excitation frequencies between 0.5 MHz and 10 MHz. Preferably, the excitation frequency of each subset of transducer elements is between 0.5 MHz and 3 MHz, or even better between 1 and 2 MHz for therapeutic applications.

The expression "transducer elements distributed randomly" should be understood to mean a random or quasi-random distribution of the transducer elements, the position of some of these transducer elements having been able to be modified from a purely random position so as to maintain a minimum space between the transducer elements. This minimum distance is, for example, of the order of 0.5 mm taken between the edges of the transducer elements. A scattered semi-random distribution of the transducer elements of each subset of transducer elements is therefore obtained, all of the transducer elements on the surface of the single support being intermingled, the distribution thus obtained being advantageously compact.

The "coverage volume" of a subset of transducer elements is defined as being the volume covered by electronic deflection of the focal point generated by this subset about its natural focal point. The "natural focal point" is defined as the point of geometrical convergence of the subset of transducer elements, the point of convergence of a subset itself being defined as the point toward which the vectors normal to the surface of each of the transducer elements that make up this subset are oriented.

Preferably, the coverage volume is the area around the natural focal point of the subset where the focal point obtained by electronic deflection has at least 50% of the acoustic power of the natural focal point of the subset of transducer elements.

Obviously, here, "point of geometrical convergence" (or natural focal point) of a subset of transducer elements must not be confused with multiple focal points that can be obtained by the action of a phased array.

The expression "target volume to be treated" should be understood to mean the volume of the target to be treated, the latter being fixed, or the total volume generated by a mobile target having a volume to be treated V.

The number of transducer elements of each subset is determined to provide sufficient energy to ensure the necrosis of the biological tissues in the coverage volume generated by this subset of transducer elements. Moreover, the expression "the transducer elements being fixed" should be understood to mean that these individual transducer elements are fixed in position and in orientation on the surface of the single support.

In particular different embodiments of this ultrasound transducer, each having its particular advantages and susceptible to numerous possible technical combinations:

The transducer elements of each subset are placed on the surface of said single support such that the points of convergence of these subsets are aligned on at least one axis.

Preferably, the target volume to be treated being mobile along a displacement axis, said points of convergence are placed on this displacement axis.

Said set comprising at least four subsets, the transducer elements of each subset are placed on the surface of said single support such that the points of convergence of at least two first subsets are placed on a first axis and the points of convergence of at least two second subsets are placed on a second axis, said first and second axes being non-parallel.

Advantageously, these axes are perpendicular.

Alternatively, the points of convergence of the subsets of the ultrasound transducer being placed along a single axis, the support of the transducer can be mounted on a rotationally mobile deck so as to displace the orientation of this axis by at least 90°, and even better 180°.

Each of said subsets of transducer elements having a specific and distinct resonance frequency, a transducer element of a subset is linked, or even wired, to a transducer element of each other subset of the phased-array ultrasound transducer of the invention, such that the choice of a given excitation frequency delivered by the control means selects and activates a single subset of transducer elements.

Preferably, transducer elements belonging to the closest different subsets will be linked, or even wired, in parallel.

It is thus possible to divide the number of cables needed at the output of the single support to power the subsets of transducer elements by N, where N is a positive integer representing the number of subsets of transducer elements of the phased-array ultrasound transducer of the invention.

As a purely illustrative example, for an ultrasound transducer comprising two subsets, each of 128 transducer elements, or 256 transducer elements on the single support, the number of cables needed to power these transducer elements from the control means is 128.

Alternatively, the control means emit a main excitation signal comprising a superposition of at least two secondary excitation signals having distinct excitation frequencies, each of said subsets of transducer elements responding to a single excitation frequency, these excitation frequencies being different for all the subsets.

Preferably, the main excitation signal being a multi-spectral signal, the secondary excitation signals are monochromatic excitation signals.

The control means are linked to each transducer element individually.

Alternatively, the control means being linked to said transducer elements by links, at least some of said links link said control means to groups of transducer elements, each group comprising at least one transducer element of at least two distinct subsets.

The transducer elements belonging to each of said groups are thus electrically connected in parallel.

The invention also targets a method for fabricating an ultrasound transducer for medical use as described previously.

According to the invention, this method comprises at least the following successive steps, said steps being performed by at least one computation unit:

a) having a single support, transducer elements defining a first subset of transducer elements intended to focus an ultrasound energy in a first coverage volume are distributed randomly on the surface of said support, b) the transducer elements of the first subset being fixed, transducer elements defining a second subset of transducer elements intended to focus an ultrasound energy in a second coverage volume distinct from said first volume are scattered on the surface of said support comprising said first subset, c) the position of each of the transducer elements of this second subset is adjusted so as to limit the array lobes which could appear in the focal plane if this subset of transducer elements included symmetries, while maintaining a minimum distance d between any two transducer elements, d) the transducer elements of each duly formed subset being fixed, steps b) and c) are repeated as necessary for each new subset of transducer elements of this transducer intended to focus an ultrasound energy in a coverage volume distinct from said other coverage volumes.

After optimization by computation of the position of the transducer elements on the surface of the single support, the single support of the transducer is produced, for example, by rapid prototyping. As a purely illustrative example, the transducer can then be produced by laser powder sintering or even by stereolithography. In line with the position of the transducer elements of the subsets, this single support may comprise channels that open out for the passage of the cables.

The single support of the transducer can thus be of a single piece made of plastic material, which makes it advantageously compatible with magnetic resonance imaging (MRI). The transducer elements, which can be piezoelectric ceramics of a single piece or an assembly of a plurality of individual ultrasound emitters, are then added and fixed onto the single support.

Advantageously, the determination of the point of geometrical convergence of each subset of transducer elements being determined by the orientation of the normal vector of each of the transducer elements, there is no longer a need for a particular form of single support, unlike the transducers of the prior art. The single support of the invention is therefore not necessarily a spherical skull cap but can advantageously be adapted to the anatomy of the target organ. As a nonlimiting example, to treat a kidney, the single support may take an elongate and incurved form. Alternatively, to treat a breast, the single support may take a cylindrical or even truncated cone form ensuring that the organ to be treated is fully covered.

As a purely illustrative example, the computation unit is a computer comprising display means.

Step c) makes it possible to take into account the placement limitations of the transducer elements of a new subset in relation to the transducer elements that are already fixed in position on the surface of the single support. The placement of the transducer elements is performed randomly.

The transducer elements of the different subsets are therefore distributed randomly by being mixed together on the surface of the single support.

The invention also targets a therapeutic treatment machine equipped with at least one ultrasound transducer for medical use as described previously.

This therapeutic treatment machine may comprise a medical imaging device such as a magnetic resonance imaging (MRI) device in order to track in real time the trend of the therapeutic treatment provided by the ultrasound transducer.

Alternatively, the imaging device may be a tomography imaging device or even an echography imaging device.

The tomography imaging device comprises an X-ray source.

The invention will be described in more detail with reference to the appended drawings in which.

Figure 1:
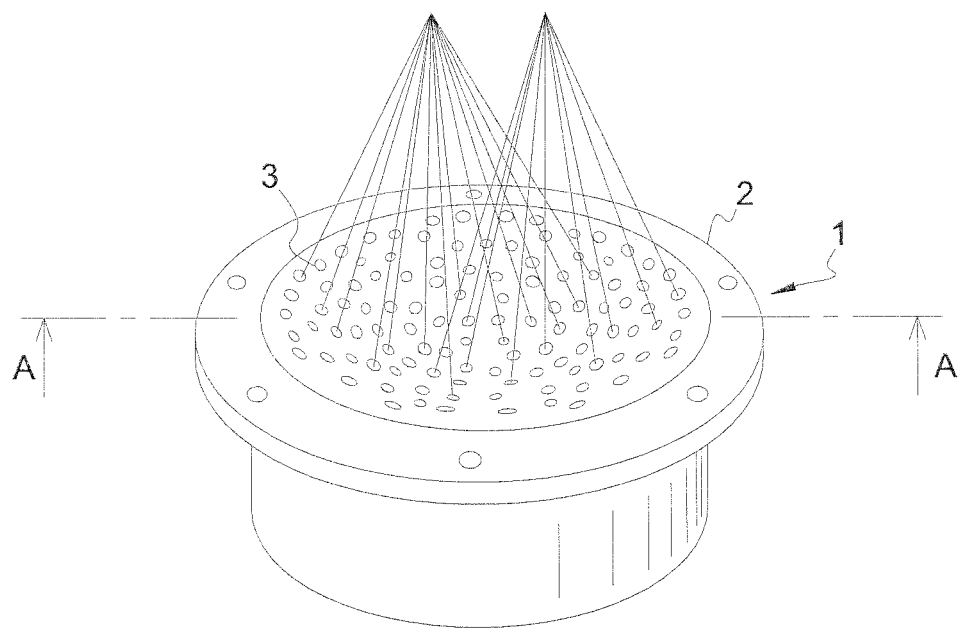
FIG. 1 is a schematic representation of an ultrasound transducer for medical use according to a preferred embodiment of the invention.
Figure 2:
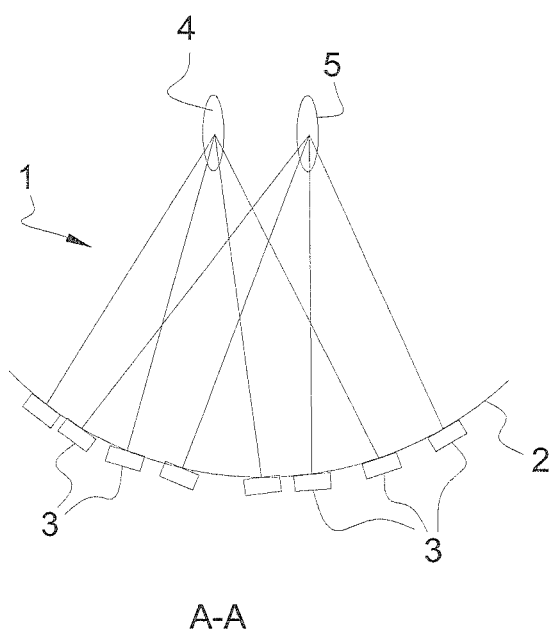
FIG. 2 is a cross-sectional view on the axis A-A of the transducer of FIG. 1.
Figure 3:
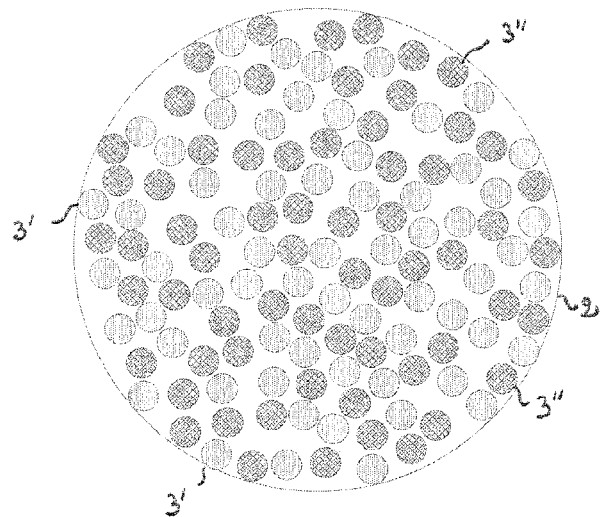
FIG. 3 is a plan view of the transducer of FIG. 1.
Figure 4:
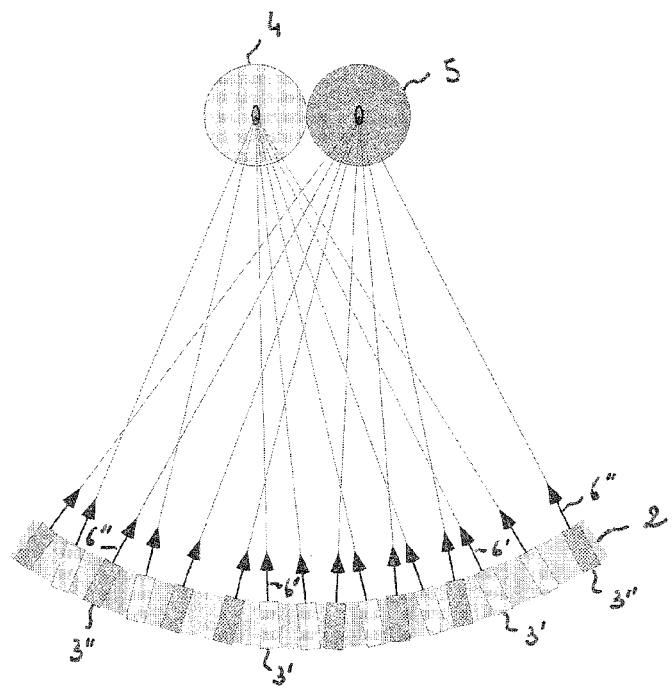
FIG. 4 is another cross-sectional view on the axis A-A of the transducer of FIG. 1.
Figure 5:
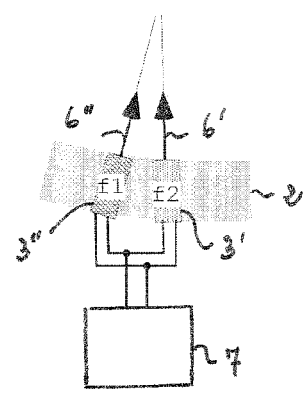
FIG. 5 is an enlarged view of FIG. 4 in which two transducer elements belonging to distinct subsets are connected in parallel.

FIGS. 1 to 5 show an ultrasound transducer for medical use according to a preferred embodiment of the invention. This ultrasound transducer 1 comprises a single support 2, hereinafter called matrix. This matrix 2 here has the form of a spherical skull cap. As a purely illustrative example, this matrix 2, which is made of plastic material, has a radius of curvature of 12 cm.

The matrix 2 is pierced with cylindrical orifices (not represented) distributed randomly on the surface of the matrix 2 and oriented in such a way that the axes of these cylindrical orifices here point toward two distinct points of convergence.

The ultrasound transducer also comprises ultrasound emitters 3 which are fixed in this matrix at the level of these cylindrical orifices so as to define two subsets of emitters.

These two subsets are intended to focus an ultrasound energy in distinct coverage volumes such that the arrangement of these two coverage volumes covers a target volume to be treated.

Each ultrasound emitter 3 is here a single-piece piezoelectric ceramic received in a rigid cylinder, this cylinder also comprising passive components for impedance matching and the connection system making it possible to link the ultrasound emitter 3 to control means (not represented) of these emitters such as a generator of excitation signals.

According to one implementation of the invention, the ultrasound emitters 3 are piezoelectric elements marketed by the company Ferroperm Piezoceramics A/S, Kvistgaard, Denmark. They have the following characteristics:

First subset of ultrasound emitters 3:
  thickness: 2 mm
  resonance frequency: 1.03 MHz
  diameter: 5 mm
  material: PZ26
Second subset of ultrasound emitters 3:
  thickness: 2.22 mm
  resonance frequency: 0.96 MHz
  diameter: 5 mm
  material: PZ26

In the simplest embodiment described above, two points of convergence are defined and two subsets of 64 cylindrical orifices are produced in the matrix 2, so as to accommodate 128 ultrasound emitters 3 pointing toward two distinct natural focal points 4, 5 separated by approximately 2.5 cm.

The two natural focal points 4, 5 are oriented in the main direction of movement of a target organ to be treated (not represented). Depending on the position of the target at a given moment, the subset of ultrasound emitters 3 offering the best capacity to focus on this target is activated with a suitable phase law, that is to say that this law takes account of the position of the target in relation to the individual ultrasound emitters. The overall coverage of the transducer (without mechanical displacement) is therefore the superposition of the coverage volumes generated by the two subsets, each subset of ultrasound emitters approximately covering a coverage volume of spherical form which here has a diameter of 3 cm.

Alternatively, the sound emitters 3 of the two subsets have slightly different resonance frequencies, such that the signals at the resonance frequency of one subset do not affect the ultrasound emitters 3 of the other subset. Thus, it is possible to wire pairs of ultrasound emitters, one from each subset, in parallel.

The number of links, or cables, needed is thus divided by two, i.e. 64 cables to connect the 128 ultrasound emitters of the transducer of FIG. 1. The selection of one of the two subsets is made by the choice of the frequency of the signal sent which corresponds to the resonance frequency of one of the two subsets.

By using spectral multiplexing, the number of generation pathways needed to power an ultrasound transducer comprising a plurality of subsets (respectively associated with different areas of the tumor) is divided by an integer number. The focal points created by the subsets of ultrasound emitters 3 can be activated either sequentially or in parallel.

Activation in parallel is made possible by the use of a generator of signals delivering multi-frequency signals. These excitation signals are, for example, the sum of a plurality of purely sinusoidal signals, each having their own phase law.

There now follows a description of a method for fabricating an ultrasound transducer according to FIGS. 1 to 5, in which
a) n transducer elements 3', 3", n here being equal to 128 purely as an illustration, are positioned on the surface of the single support,
b) each duly positioned transducer element 3', 3" is randomly assigned to a subset of transducer elements (solid circle, shaded circle), the number of subsets being given by the number of desired points of geometrical convergence 4, 5. Since this number here is equal to 2, each transducer element 3', 3" is allocated randomly to one of the two subsets, i.e. 64 elements per subset of transducer elements.
c) the normal vector 6', 6" of each of said transducer elements 3', 3" is oriented as a function of the point of geometrical convergence 4, 5 of the subset to which said transducer element 3', 3" has been assigned,
d) the transducer elements 3', 3" are connected to control means 7 to control these transducer elements 3', 3" independently of one another.

The assignment of at least some transducer elements 3', 3" is adjusted as necessary to obtain a uniform distribution of the subsets of transducer elements on the surface of the single support 2.

Preferably, in step a), as many transducer elements as necessary are positioned such that the aggregate surfaces of all of these transducer elements represent at least fifty percent (50%) of the surface of said single support.

Alternatively, and in the context of an ultrasound transducer comprising only two subsets of transducer elements, this transducer can be fabricated by randomly distributing the transducer elements in pairs.

Each subset of transducer elements 3', 3" having a specific and distinct resonance frequency, $f_1$ and $f_2$, a transducer element 3' of a first subset (solid circle) is connected in parallel to a transducer element 3" of the second subset (shaded circle) such that the choice of a given excitation frequency $f_1$ or $f_2$ delivered by the control means 7 makes it possible to select one of the two subsets of transducer elements.

The invention claimed is:
1. A phased-array ultrasound transducer for medical use, said transducer comprising:
  a single support (2);
  a set of transducer elements (3) distributed randomly on a surface of said single support (2), said transducer elements (3) being fixed, wherein said set of transducer elements comprises at least two subsets of transducer elements (3), each of said at least two subsets of transducer elements (3) having a distinct point of geometrical convergence in a distinct coverage volume (4, 5), wherein said coverage volumes cover a target volume to be treated; and
  control means for activating said transducer elements (3) independently of one another,
  wherein all the randomly distributed transducer elements in said at least two subsets are intermingled with each other on said single support.
2. The transducer as claimed in claim 1, wherein the transducer elements (3) of each of said at least two subsets are arranged on the surface of said single support (2) such that the points of convergence of these at least two subsets are aligned on at least one axis.

3. The transducer as claimed in claim 2, wherein said set of transducer elements comprises at least four subsets of transducer elements, the transducer elements (3) of each of said at least four subsets being arranged on the surface of said single support (2) such that the points of convergence of at least two first subsets are on a first axis and the points of convergence of at least two second subsets are on a second axis, said first and second axes being non-parallel.

4. The transducer as claimed in claim 1, wherein said points of convergence of the at least two subsets are on a same axis.

5. The transducer as claimed in claim 1, wherein each of said at least two subsets of transducer elements has a specific and distinct resonance frequency, and wherein each of the transducer elements of one of said at least two subsets is linked to one of the transducer elements of each of the other said at least two subsets of the phased-array ultrasound transducer such that a given excitation frequency, delivered by the control means, activates a single one of the at least two subsets of transducer elements.

6. The transducer as claimed in claim 1, wherein said control means is linked to said transducer elements (3) by links, at least some of said links link said control means to groups of the transducer elements (3), each of the groups comprising at least one transducer element of at least two distinct ones of the at least two subsets.

7. The transducer as claimed in claim 1, wherein an aggregate of surface areas of all the transducer elements represent at least fifty percent (50%) of a surface area of said single support.

8. The transducer as claimed in claim 1, wherein said single support has a shape chosen from the group consisting of a truncated cone, a paraboloid, a cylinder, an elongated form, and an incurved form.

9. A therapeutic treatment machine equipped with at least one ultrasound transducer for medical use as claimed in claim 1.

10. A method for fabricating an ultrasound transducer as claimed in claim 1, characterized in that it comprises at least the following successive steps, said steps being performed by at least one computation unit:
  a) having a single support (2), transducer elements (3) defining a first subset of transducer elements (3) intended to focus an ultrasound energy in a first coverage volume (4, 5) are distributed randomly on the surface of said support (2),
  b) the transducer elements (3) of the first subset being fixed, transducer elements (3) defining a second subset of transducer elements (3) intended to focus an ultrasound energy in a second coverage volume (4, 5) distinct from said first volume are scattered on the surface of said support (2) comprising said first subset,
  c) the position of each of the transducer elements (3) of this second subset is adjusted so as to limit the array lobes which could appear in the focal plane if this subset of transducer elements (3) included symmetries, while maintaining a minimum distance d between any two transducer elements,
  d) the transducer elements (3) of each duly formed subset being fixed, steps b) and c) are repeated as necessary for each new subset of transducer elements (3) intended to focus an ultrasound energy in a coverage volume (4, 5) distinct from said other coverage volumes.

11. A method for fabricating an ultrasound transducer as claimed in claim 1, characterized in that it comprises at least the following successive steps, some of said steps being performed by at least one computation unit:
  a) n transducer elements are positioned on the surface of a single support,
  b) each duly positioned transducer element is randomly assigned to a subset of transducer elements, the number of subsets being given by the number of desired points of geometrical convergence,
  c) the normal vector of each of said transducer elements is oriented as a function of the point of geometrical convergence of the subset to which said transducer element has been assigned.

12. The method as claimed in claim 11, characterized in that the assignment of at least some transducer elements is adjusted to obtain a uniform distribution of said subsets of transducer elements on the surface of said single support.

13. The method as claimed in claim 12, characterized in that, in step a), as many transducer elements are placed such that the aggregate surfaces of all of these transducer elements represent at least fifty percent (50%) of the surface of said single support.

14. The method as claimed in claim 11, characterized in that, in step a), as many transducer elements are placed such that the aggregate surfaces of all of these transducer elements represent at least fifty percent (50%) of the surface of said single support.

* * * * *